(12) United States Patent
Yau et al.

(10) Patent No.: US 7,909,607 B2
(45) Date of Patent: Mar. 22, 2011

(54) METHOD FOR DESIGNING A DIGITAL ABUTMENT FOR DENTAL IMPLANT

(75) Inventors: Hong-Tzong Yau, Chiayi County (TW); Chuan-Chu Kuo, Chiayi County (TW); Jiun-Ren Chen, Yunlin County (TW); Fu-Chieh Hsiao, Chiayi (TW)

(73) Assignee: Pou Yu Biotechnology Co., Ltd., Chang Hwa Hsien (TW)

( * ) Notice: Subject to any disclaimer, the term of this patent is extended or adjusted under 35 U.S.C. 154(b) by 279 days.

(21) Appl. No.: 12/155,695

(22) Filed: Jun. 9, 2008

(65) Prior Publication Data
US 2009/0111071 A1   Apr. 30, 2009

(30) Foreign Application Priority Data
Oct. 25, 2007   (TW) ............................... 96140139 A

(51) Int. Cl.
*A61C 8/00*   (2006.01)
(52) U.S. Cl. ........................................ 433/223; 433/173
(58) Field of Classification Search .................. 433/172, 433/173, 174, 213, 214, 223
See application file for complete search history.

(56) References Cited

U.S. PATENT DOCUMENTS

| | | | | |
|---|---|---|---|---|
| 5,527,182 A * | 6/1996 | Willoughby | ................... | 433/172 |
| 5,674,069 A * | 10/1997 | Osorio | ........................ | 433/172 |
| 5,989,029 A * | 11/1999 | Osorio et al. | ................. | 433/173 |
| 6,231,342 B1 * | 5/2001 | Osorio et al. | ................. | 433/173 |
| 6,283,753 B1 * | 9/2001 | Willoughby | ................... | 433/172 |
| 6,814,575 B2 * | 11/2004 | Poirier | ........................... | 433/75 |
| 2004/0120781 A1 * | 6/2004 | Luca et al. | ..................... | 409/84 |
| 2004/0197737 A1 * | 10/2004 | Uckelmann et al. | .......... | 433/173 |
| 2006/0106484 A1 * | 5/2006 | Saliger et al. | ................. | 700/182 |
| 2007/0154868 A1 * | 7/2007 | Scharlack et al. | ............ | 433/215 |
| 2007/0203599 A1 * | 8/2007 | Shibata et al. | .................. | 700/98 |

\* cited by examiner

*Primary Examiner* — Ralph A Lewis
(74) *Attorney, Agent, or Firm* — Bacon & Thomas, PLLC

(57) ABSTRACT

A method for designing a digital abutment for a dental implant includes the steps of: a) implant planning where implant planning is initiated based on digital data obtained from the patient and loaded into a computer system to enable an implant fixture to be implanted at the implant site in the best position, b) establishment of digital reference abutment where a digital reference abutment is established at the implant site and positioned on the implant fixture, c) adjustment of the digital reference abutment where the digital reference abutment has a subgingival part and a supragingival part at the top side of the subgingival part, and the angle between the subgingival part and the supragingival part is adjusted based on the best prosthesis position, and d) finish of digital abutment where the digital reference abutment becomes a digital abutment for placement after the adjustment.

12 Claims, 10 Drawing Sheets

METHOD FOR DESIGNING A DIGITAL ABUTMENT FOR DENTAL IMPLANT

BACKGROUND OF THE INVENTION

1. Field of the Invention

The present invention relates to dental implant techniques and more particularly, to a method for designing a digital abutment for dental implant.

2. Description of the Related Art

Existing dental implant planning software allows a dentist to plan in a computer a suitable location on the alveolar bone for the positioning of the implant fixture. However, because of aesthetic considerations, bite accuracy, or poor alveolar bone condition, the result of implant planning may be not optimal. At this time, the dentist can make improvements by means of an angled abutment. However, selection of an abutment after dental implant planning using conventional techniques may encounter certain problems.

Commercial standard abutments have fixed angles. A dentist is unable select the ideal abutment that fits the bite angle perfectly based on the angle of the implant fixture, causing problems in the follow-up fabrication of the artificial tooth. After implantation, the artificial tooth may not have the esthetics or may not regain satisfactory biting function, and the problem of the bite angle after implantation of the implant fixture may result in osseointegration failure and dental implant failure.

SUMMARY OF THE INVENTION

The present invention has been accomplished under the circumstances in view. It is one object of the present invention to provide a method for designing a digital abutment for dental implant that greatly improves the sense of beauty of the implanted artificial tooth.

It is another object of the present invention to provide a method for designing a digital abutment for a dental implant that greatly reduces the chances of osseointegration failure after the dental implant.

It is still another object of the present invention to provide a method for designing a digital abutment for dental implant that greatly improves the cross bite function of the implanted artificial tooth.

It is still another object of the present invention to provide a method for designing a digital abutment for a dental implant fixture that facilitates the follow-up fabrication of the artificial tooth.

To achieve this and other objects of the present invention, the method for designing a digital abutment for a dental implant fixture comprises the steps of: a) implant planning where implant planning is initiated based on digital data obtained from the patient and loaded into a computer system to enable an implant fixture to be implanted at the implant site in the best position, b) establishment of a digital reference abutment where the digital reference abutment is established at the implant site and positioned on the implant fixture, c) adjustment of a digital reference abutment where the digital reference abutment has a subgingival part and a supragingival part at the top side of the subgingival part, and the angle between the subgingival part and the supragingival part is adjusted based on the best prosthesis position, and d) finish of digital abutment where the digital reference abutment becomes a digital abutment for placement after the adjustment, and the digital abutment is outputted to a fabrication system for the fabrication of a finished abutment product.

DETAILED DESCRIPTION OF THE INVENTION

Figure 1:
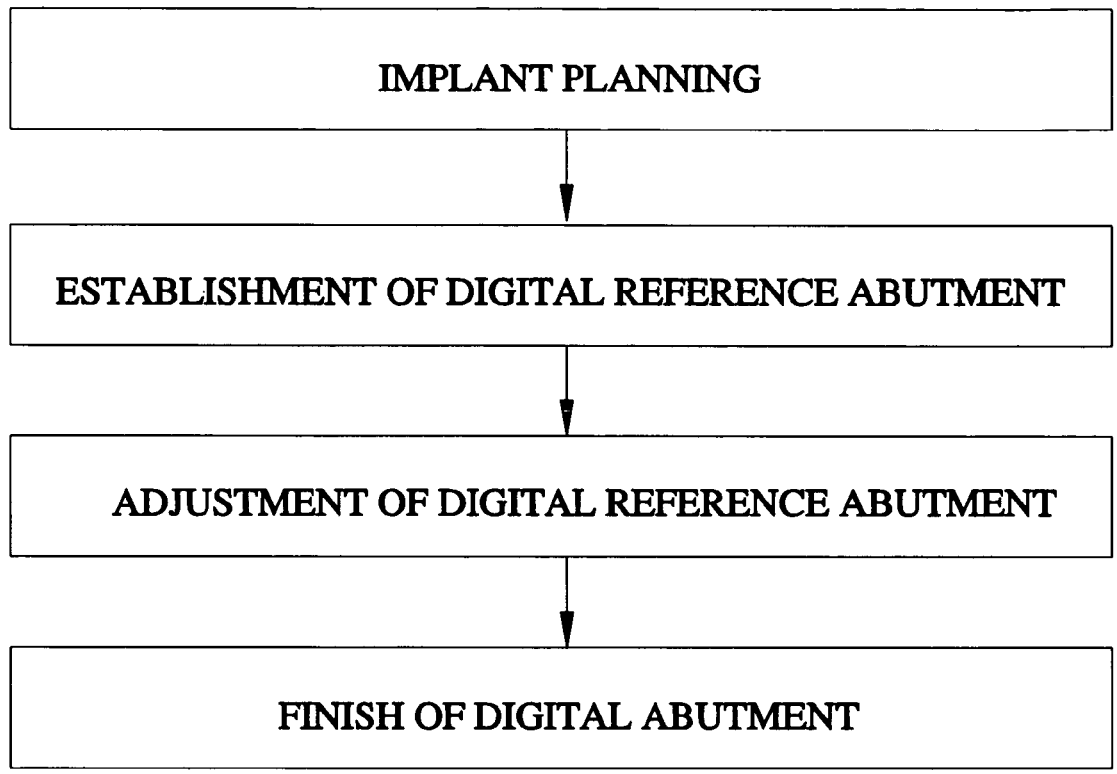
FIG. 1 is a flow chart of a method for designing a digital abutment for a dental implant fixture in accordance with a first embodiment of the present invention.
Figure 2:
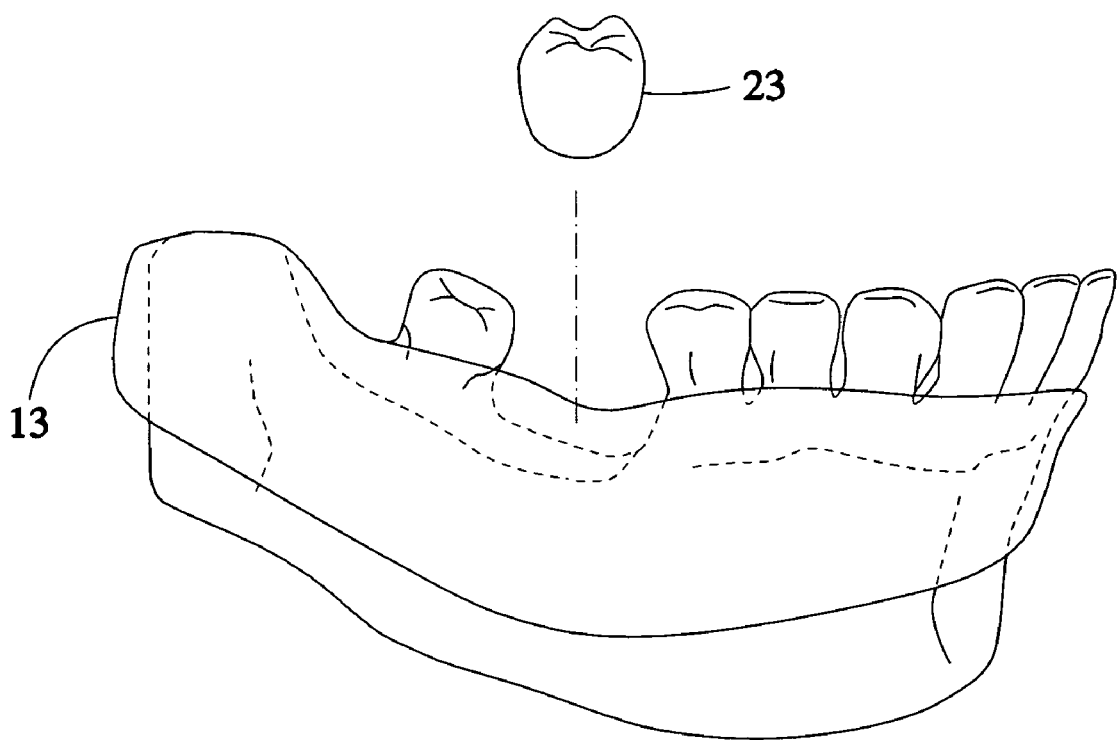
FIG. 2 is a schematic side view of the first embodiment of the present invention, showing the configuration of the digital gum and the digital crown.
Figure 3:
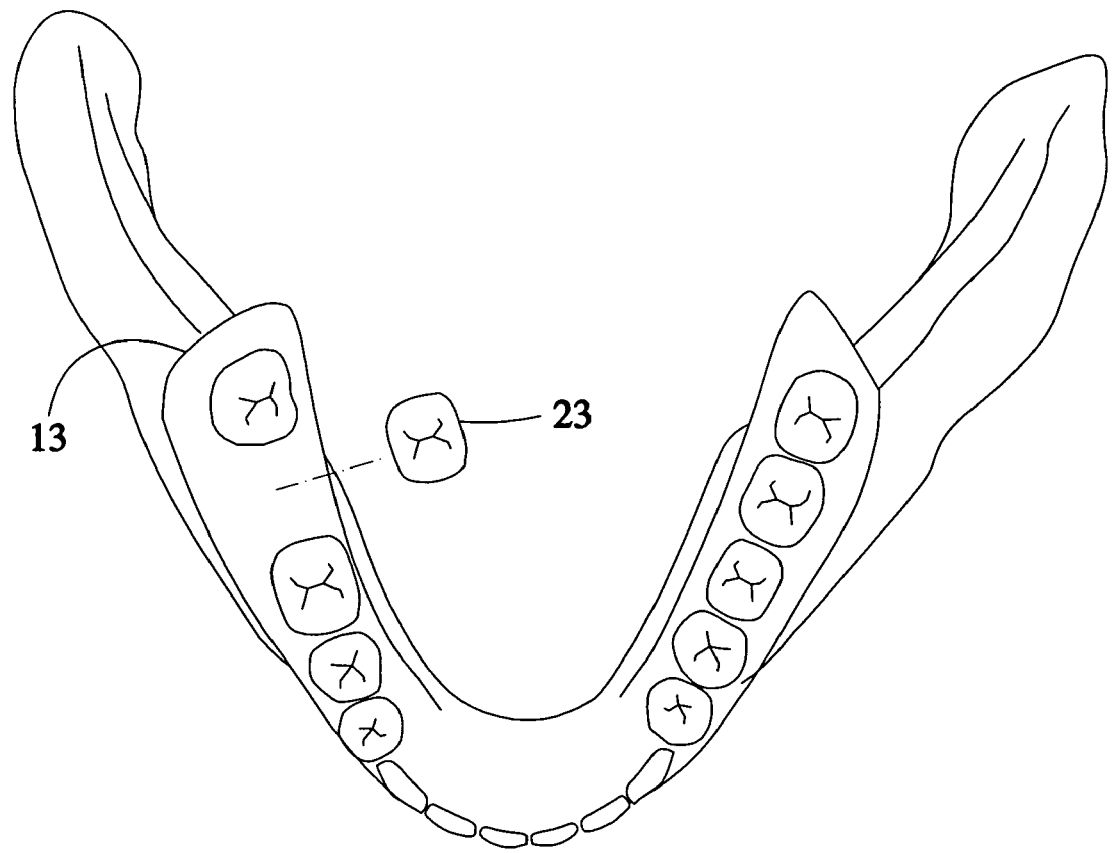
FIG. 3 is a schematic top view of the first embodiment of the present invention, showing the configuration of the digital gum and the digital crown.
Figure 4:
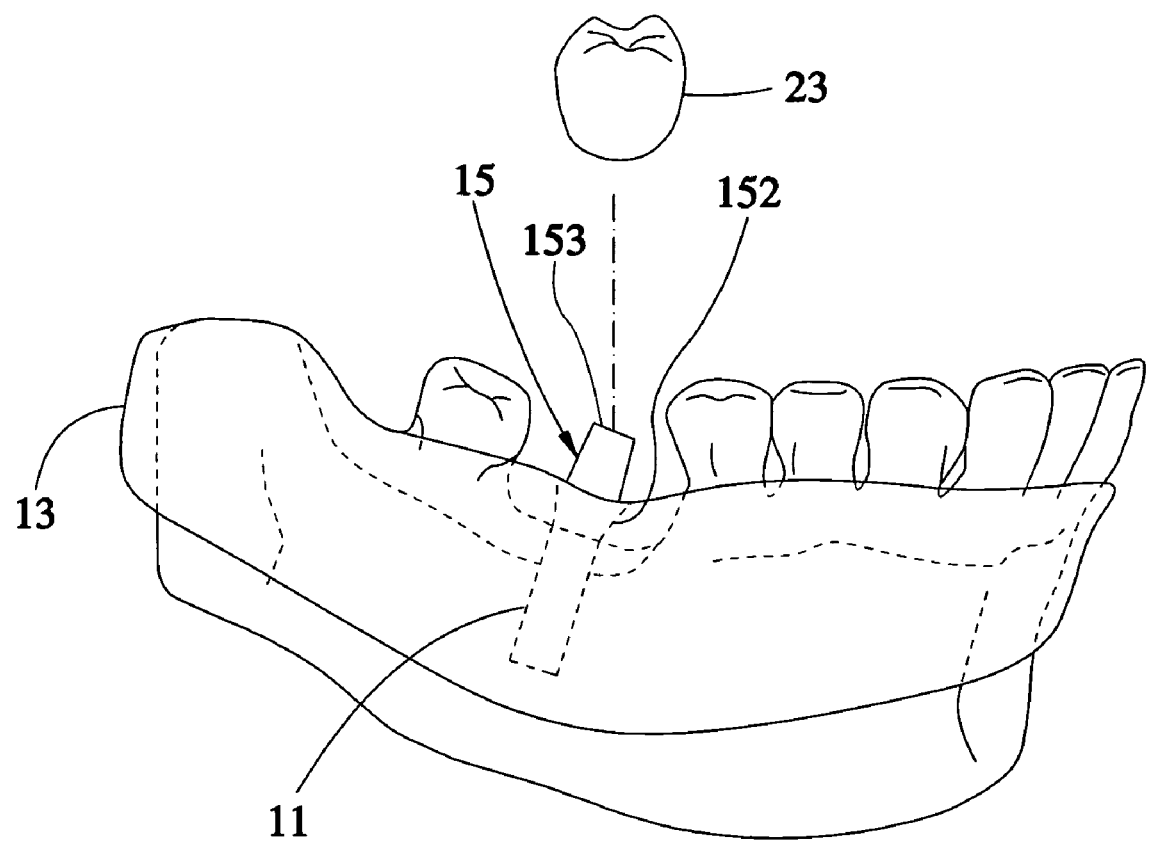
FIG. 4 is a schematic side view of the first embodiment of the present invention, showing the status of the digital reference abutment at the implant site before adjustment.
Figure 5:
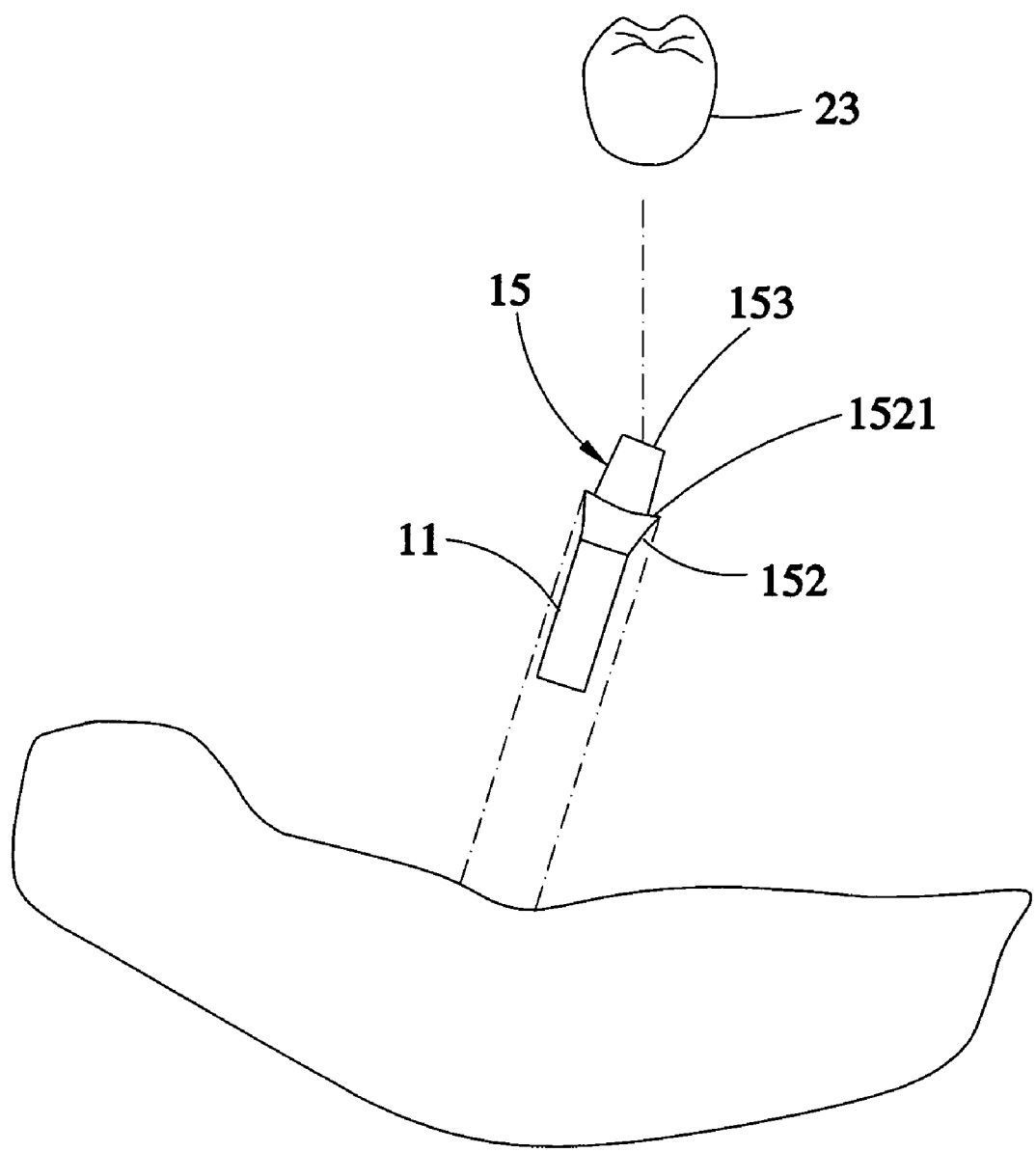
FIG. 5 is an exploded view of FIG. 4.
Figure 6:
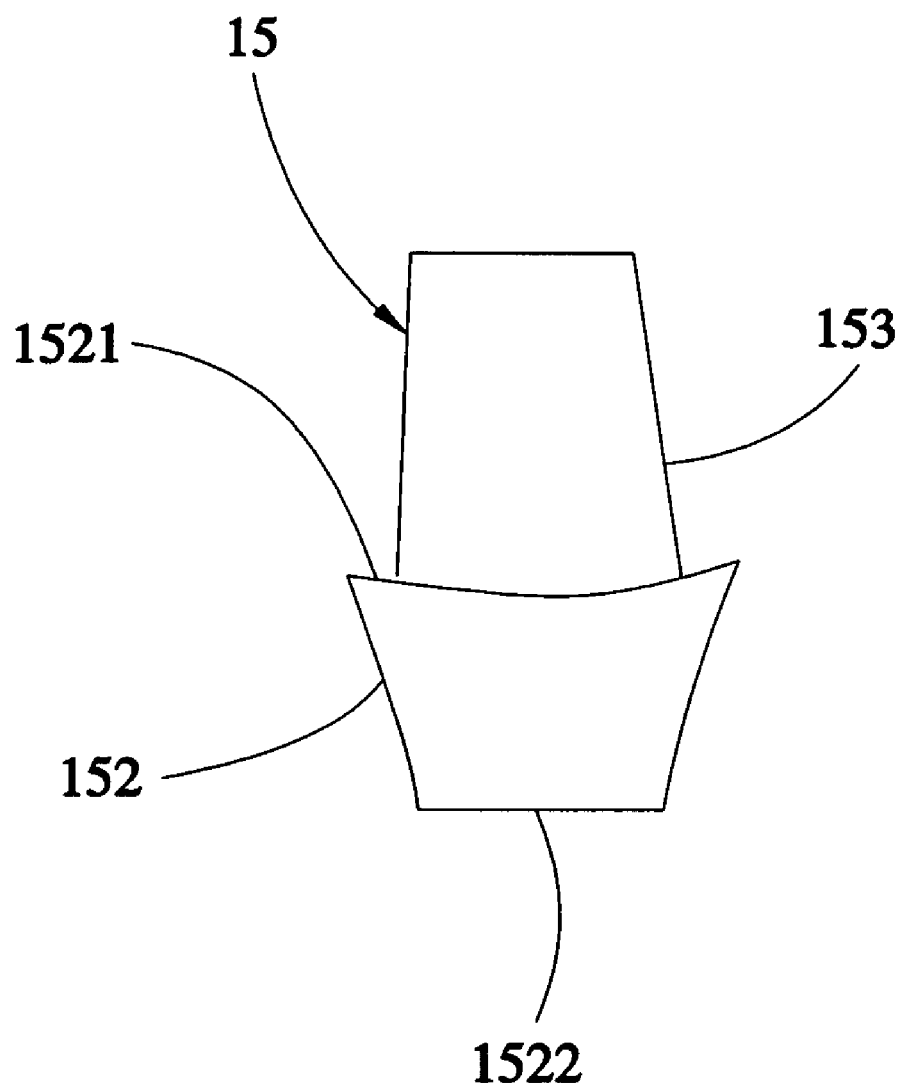
FIG. 6 is a schematic side view of the first embodiment of the present invention, showing the configuration of the digital reference abutment.
Figure 7:
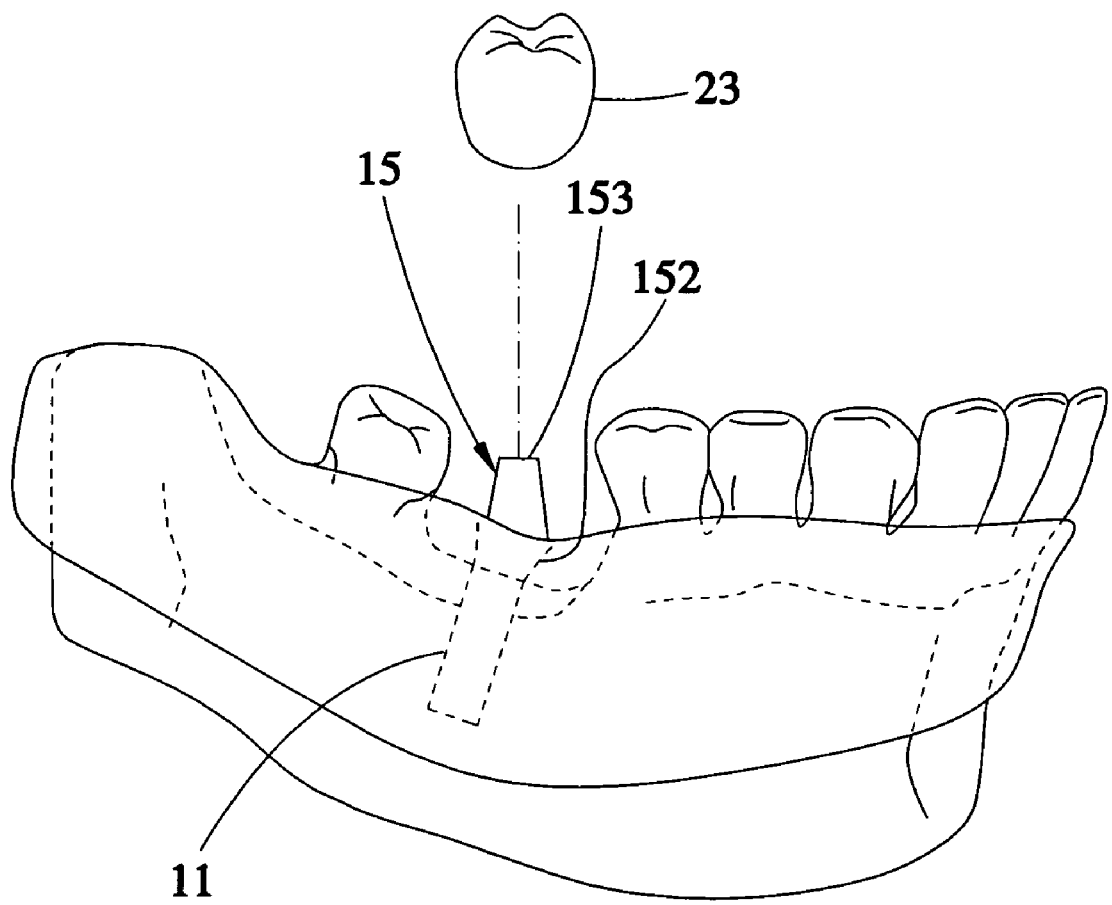
FIG. 7 corresponds to FIG. 4, showing the status of the digital reference abutment at the implant site after adjustment.
Figure 8:
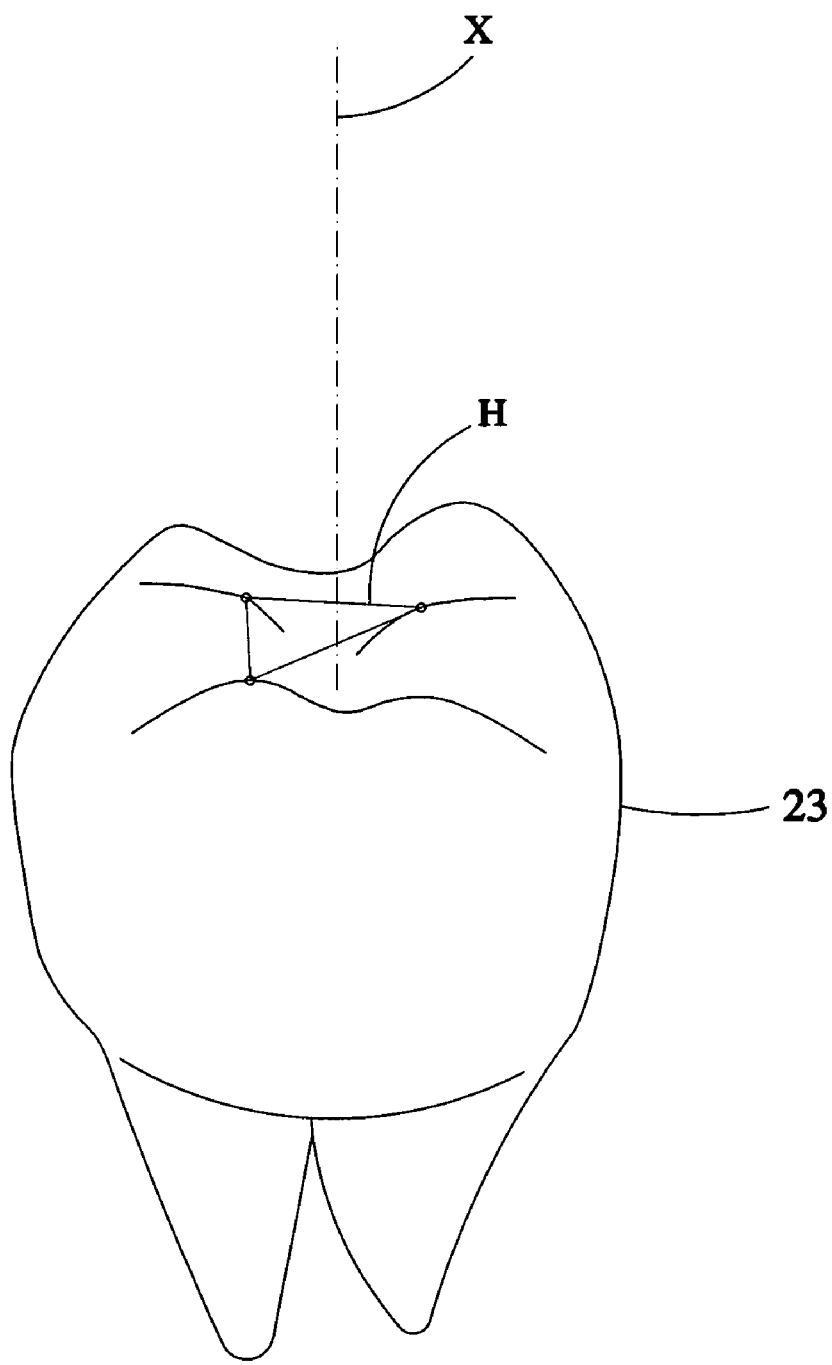
FIG. 8 is a schematic drawing of the first embodiment of the present invention, showing the stress direction of the digital crown of the digital abutment after adjustment.
Figure 9:
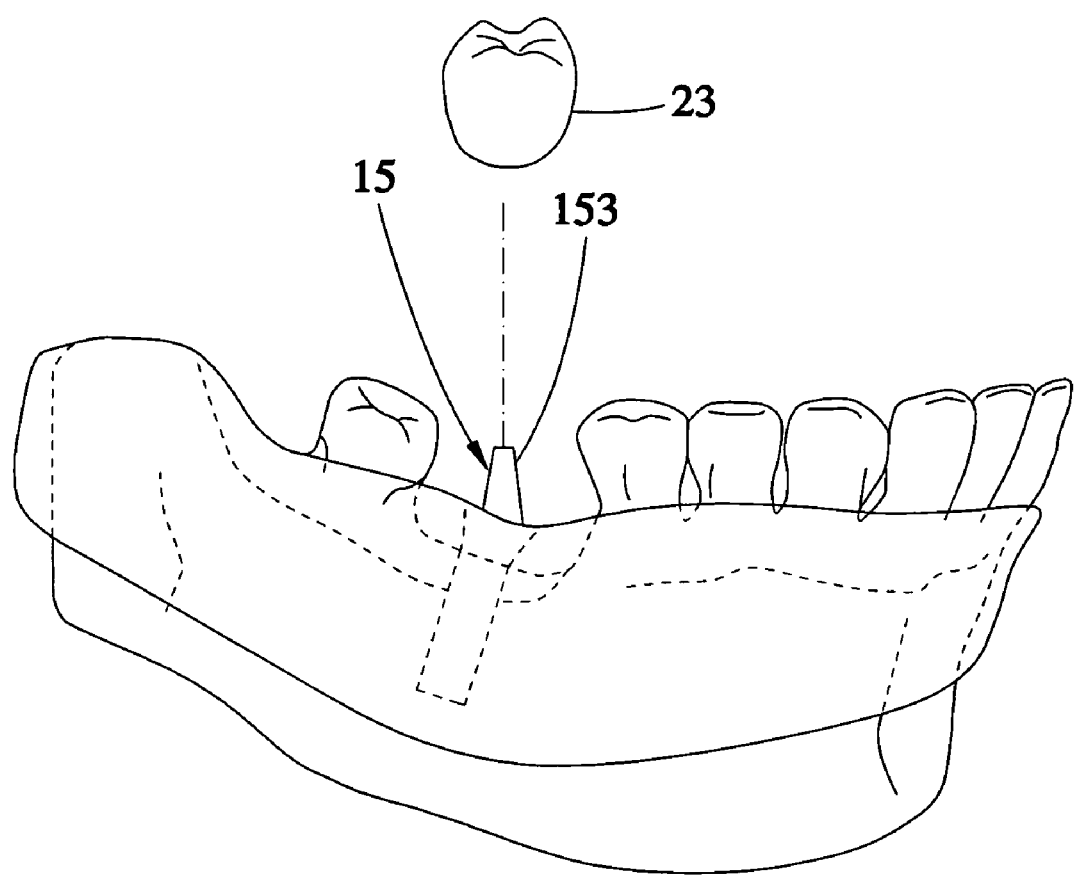
FIG. 9 is a schematic side view of the first embodiment of the present invention, showing the relatively smaller size status of the digital reference abutment at the implant site after adjustment.

Referring to FIG. 1, a method for designing a digital abutment for a dental implant fixture in accordance with a first embodiment of the present invention includes the steps of:

a) Implant planning: As shown in FIGS. 2 and 3, initiate implant planning based on the digital data obtained from the patient and loaded into the computer system to enable the digital implant fixture 11 (see FIG. 4) to be implanted at the implant site in the best position. The computer has the data of the digital oral cavity model of the patient. The data of the digital oral cavity model includes a digital gum 13 and a digital crown 23. The digital gum 13 and the digital crown 23 can be loaded from a digital database (not shown) of the computer system. Alternatively, the digital data can be loaded by means of scanning a gum/crown model made subject to the configuration of the oral cavity of the patient.

b) Establishment of digital reference abutment: As shown in FIGS. 4. about. 6, a digital reference abutment 15 is loaded from the digital database of the computer system and established at the digital implant fixture 11.

c) Adjustment of digital reference abutment: The digital reference abutment 15 has a subgingival part 152 and a supragingival part 153 at the top side of the subgingival part 152. The optimal angle between the subgingival part 152 and the supragingival part 153 is adjusted based on the best prosthesis position. The size of the supragingival part 153 is adjusted based on the size of the digital crown 23. The subgingival part 152 has a top surface 1521 and a bottom surface, namely, the interface 1522. The top surface 1521 is obtained by means of drawing a gum line on the digital gum 13 that matches the surface configuration of the digital gum 13 at the prosthesis position. The supragingival part 153 is formed upwards from the top surface 1521 of the subgingival part 152. The configuration of the interface 1522 fits the top surface of the digital implant fixture 11 so that subgingival part 152 and the digital implant 11 can be positively bonded together. The adjustment of the angle of the subgingival part 152 and the supragingival part 153 takes the consideration of the stress direction of the bite into account so that adjustment of the best angle can be obtained. FIG. 7 shows the status after adjustment. The stress direction of the bite is the axial direction of the stress produced during bite on the digital crown 23. As shown in FIG. 8, the definition of the axial direction of the stress is described hereinafter. Take three cusp points from the digital crown 23 to define a bite plane H, and then define a straight line X perpendicular to the bite plane H subject to the reference point at the center groove of the occlusal surface. This straight line X is the axial direction of the stress of the digital crown. Further, during the aforesaid adjustment step, if the prosthesis site of the crown 23 causes bias of the supragingival part 153, an uneven stress problem may occur during installation of the real crown in the crown 23. This problem can be eliminated by means of an adjustment. As shown in FIG. 9, the size of the supragingival part 153 of the digital reference abutment 15 is adjusted (for example, reduced), and the size of the digital crown 23 is relatively adjusted to fit the supragingival part 153, thereby eliminating the installation problem due to bias of the supragingival part 153.

d) Finish of digital abutment: After the adjustment is made, the digital reference abutment 15 becomes a digital abutment for an implant fixture, as shown in FIG. 7, and this digital abutment is outputted to a fabrication system for the fabrication of a finished abutment product.

Subject to the aforesaid procedure, a digital dental implant technique is employed to initiate implant planning before the actual dental implant surgery and to establish the digital gum 13 and the distal crown 23, and then to generate the adjusted subgingival part 152 and supragingival part 153 based on the digital gum 13 and the distal crown 23, thereby forming the digital abutment. The digital abutment is then outputted to a fabrication system for the fabrication of a finished abutment product. The finished abutment product can be used directly on the implant fixture, and the stress direction of the bite of this abutment can facilitate the follow-up fabrication of the desired artificial tooth.

Figure 10:
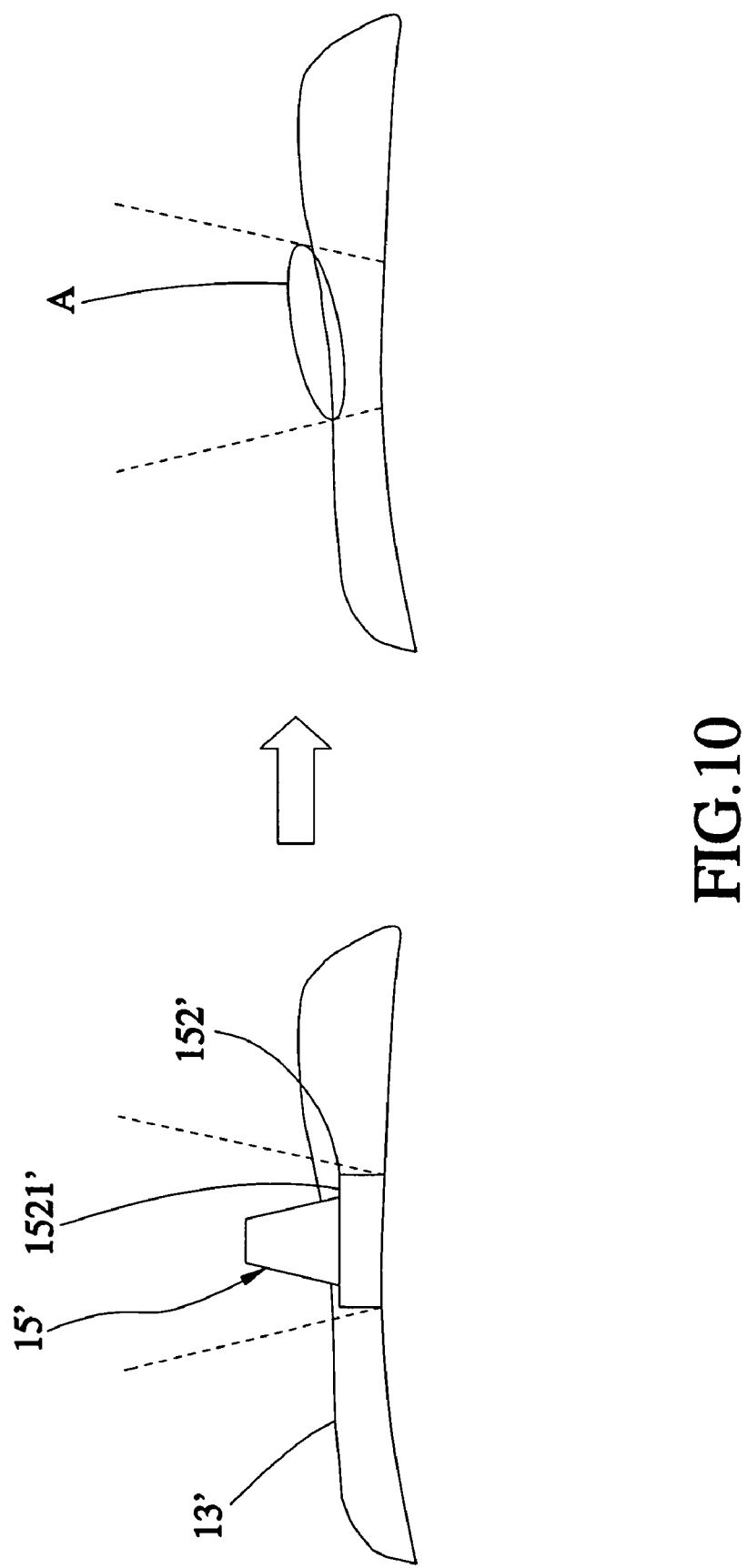
FIG. 10 is a schematic drawing showing a method for designing a digital abutment for a dental implant fixture in accordance with a second embodiment of the present invention.

FIG. 10 is a schematic drawing showing a method for designing a digital abutment for a dental implant fixture in accordance with a second embodiment of the present invention. This second embodiment is substantially similar to the aforesaid first embodiment with the exception that:

In step c), the configuration of the top surface of the subgingival part 152' is determined based on the closed area A of the intersection between the upward extension of the periphery of the reference of the subgingival part 152' of the digital reference abutment 15' and the digital gum 13'. This closed area A is the configuration of the top surface 1521' of the subgingival part 152' of the digital reference abutment 15'. The other steps and the achievable function of this second embodiment are the same as the aforesaid first embodiment.

As stated above, the invention allows adjustment of the angle of the digital abutment to facilitate fabrication of a suitable finished abutment product, assuring high accuracy of the bite angle of the follow-up implant and excellent function of cross bite, facilitating the follow-up artificial fabrication, and improving the sense of beauty of the implanted artificial tooth. Therefore, the invention eliminates the problems of osseointegration failure and dental implant failure as encountered in conventional dental implant techniques.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A method for designing a digital abutment for a dental implant fixture, comprising the steps of:
   a) using digital data obtained from a patient and loaded into a computer system to determine an optimum position for placing an implant fixture at an implant site on the patient by using a digital implant fixture and a digital implant site;
   b) establishing a digital reference abutment, wherein the digital reference abutment is established at the digital implant site and positioned on the digital implant fixture;
   c) adjusting the digital reference abutment, wherein said digital reference abutment has a subgingival part and a supragingival part on top of said subgingival part, and an angle between said subgingival part and said supragingival part is adjusted based on an optimum prosthesis position; and
   d) finalizing adjustment of the digital abutment, wherein said digital reference abutment after adjustment is used for making a digital abutment for placement on the patient.

2. The method for designing a digital abutment for a dental implant fixture as claimed in claim 1, wherein during step c), the adjustment of the angle between said subgingival part and said supragingival part is determined based on the compressive stresses in the direction of the bite.

3. The method for designing a digital abutment for a dental implant fixture as claimed in claim 1, wherein during step a), said computer system has stored therein the data of a model of the oral cavity of a patient, and the data of said oral cavity model comprising a digital gum and a digital crown.

4. The method for designing a digital abutment for a dental implant fixture as claimed in claim 3, wherein during step c), the adjustment of the angle between said subgingival part and said supragingival part of the digital abutment is determined based on the compressive stress in the direction of the bite.

5. The method for designing a digital abutment for a dental implant fixture as claimed in claim 4, wherein said stress direction is the axial direction of the stress produced during bite on said digital crown.

6. The method for designing a digital abutment for a dental implant fixture as claimed in claim 5, wherein the axial direction of the compressive stress produced during bite on said digital crown is determined by taking three cusp points from said digital crown to define an occlusal plane and then defining a straight line perpendicular to said occlusal plane based on the reference point at the center groove of the occlusal surface of said digital crown, and this straight line is the axial direction of the compressive stress produced during bite on said digital crown.

7. The method for designing a digital abutment for a dental implant fixture as claimed in claim 3, wherein during step c), the size of said supragingival part of said digital abutment is adjusted based on the size of said digital crown.

8. The method for designing a digital abutment for a dental implant fixture as claimed in claim 3, wherein during step c), said subgingival part of said digital abutment has a top surface and an interface opposite to said top surface, and said supragingival part is formed upwards from the top surface of said subgingival part.

9. The method for designing a digital abutment for a dental implant fixture as claimed in claim 8, wherein the configuration of said interface of said subgingival part of digital abutment securely connects to the top surface of said digital implant fixture.

10. The method for designing a digital abutment for a dental implant fixture as claimed in claim 8, wherein the configuration of the top surface of said subgingival part is determined by the gum line of said digital gum.

11. The method for designing a digital abutment for a dental implant fixture as claimed in claim 8, wherein the configuration of the top surface of said subgingival part is determined based on the closed area of the intersection between an upward extension of the periphery of the interface of said subgingival part of said digital reference abutment and said digital gum, and this closed area is the configuration of the top surface of said subgingival part of said digital reference abutment.

12. The method for designing a digital abutment for a dental implant fixture as claimed in claim 1, wherein during step d), said digital abutment is outputted to a fabrication system for the fabrication of a finished abutment product.

* * * * *